United States Patent
Erdmann et al.

(10) Patent No.: US 8,716,536 B2
(45) Date of Patent: May 6, 2014

(54) PROCESS FOR THE PREPARATION OF DIRECTLY COMPRESSIBLE δ-MANNITOL

(75) Inventors: Martin Erdmann, Gross-Gerau (DE); Walter Hamm, Weiterstadt (DE); Eugen Schwarz, Wasserburg (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/994,235

(22) PCT Filed: Nov. 17, 2011

(86) PCT No.: PCT/EP2011/005801
§ 371 (c)(1),
(2), (4) Date: Jun. 14, 2013

(87) PCT Pub. No.: WO2012/079671
PCT Pub. Date: Jun. 21, 2012

(65) Prior Publication Data
US 2013/0261346 A1  Oct. 3, 2013

(30) Foreign Application Priority Data

Dec. 17, 2010  (EP) .................................... 10015770

(51) Int. Cl.
*C07C 31/26*  (2006.01)
(52) U.S. Cl.
USPC ........................................ 568/852; 568/868
(58) Field of Classification Search
USPC ................................................ 568/852, 868
See application file for complete search history.

(56) References Cited

U.S. PATENT DOCUMENTS

| | | |
|---|---|---|
| 3,145,146 A | 8/1964 | Lieberman et al. |
| 6,503,918 B2 | 1/2003 | Yoshinari et al. |
| 6,845,571 B1 | 1/2005 | Schwarz et al. |
| 6,998,481 B2 | 2/2006 | Erdmann et al. |
| 6,998,482 B2 | 2/2006 | Erdmann et al. |
| 2002/0107420 A1 | 8/2002 | Yoshinari et al. |
| 2003/0114717 A1 | 6/2003 | Erdmann et al. |
| 2005/0008693 A1 | 1/2005 | Erdmann et al. |
| 2009/0148524 A1 | 6/2009 | Higuchi et al. |

FOREIGN PATENT DOCUMENTS

| | | |
|---|---|---|
| DE | 19927537 A1 | 12/2000 |
| EP | 1319644 A1 | 6/2003 |
| EP | 1967211 A1 | 9/2008 |
| WO | 97/38960 A1 | 10/1997 |
| WO | 20041020648 A1 | 3/2004 |

OTHER PUBLICATIONS

International Search Report for PCT/EP2011/005801 (Jun. 22, 2012).
W.L. Hulse et al., "The Characterization and Comparison of Spray-Dried Mannitol Samples", Drug Development and Industrial Pharmacy, vol. 35, No. 6 (2009) pp. 712-718.

*Primary Examiner* — Elvis O Price
(74) *Attorney, Agent, or Firm* — Millen, White, Zelano & Branigan, P.C.

(57) ABSTRACT

The present invention relates to a process for the preparation of directly compressible mannitol having a content of the δ modification of greater than 90%.

22 Claims, 3 Drawing Sheets

PROCESS FOR THE PREPARATION OF DIRECTLY COMPRESSIBLE δ-MANNITOL

The present invention relates to a process for the preparation of directly compressible mannitol having a content of the δ modification of greater than 90%, in particular greater than 95%.

In the production of tablets, D-mannitol can be employed as excipient material for an active compound. To this end, D-mannitol is usually converted into a granular material in a plurality of process steps in order to enable it to be handled for tablet pressing and at the same time to facilitate binding-in of active compound. Interim checks enable the process to be carried out in a controlled manner here.

U.S. Pat. No. 3,145,146 A discloses a spray-drying process by means of which mannitol is obtained in the form of fine particles having an average diameter of from 5 to 150 μm. A mannitol solution is spray-dried by atomisation into a stream of hot gas. The particles obtained are separated off by suitable measures.

It has also been disclosed that granular D-mannitol can be prepared by granulation in a fluidised bed, in which the stream of process air flows through a specially shaped impingement plate and thus produces a fluidised bed comprising solid starting material. The spray liquid passes into the fluidisation space in finely divided form through a nozzle system. The fluidising particles are wetted, the surface is partially dissolved, and the particles adhere together and dry in the stream of air which carries them to the outlet of the fluidised bed. Solid is withdrawn continuously at the end of the fluidised bed. At the same time, a smaller amount of the bed is formed at the inlet by recycled solid, onto which spray liquid is finely distributed. A filter system prevents dust from leaving the fluidised bed, and only granule particles which have a minimum size are withdrawn at the outlet. In addition, solid particles which have a more or less random shape form in a fluidised bed of this type. Corresponding plants are marketed by various manufacturers.

The preparation of granular mannitol is usually followed by a process step by means of which a granular material having a uniform particle size distribution is obtained. This process step can include both grinding and screening (classification) of the granular material. In the case of the use of mannitol as excipient material for pharmaceutical active compounds, any additional process step in the preparation represents to the person skilled in the art a possible risk of the introduction of undesired impurities into the product.

It is known from the literature that D-mannitol can exist in polymorphic crystal forms; to be precise in the α, β and δ forms. The definitions and characterisations used here correspond to the classifications of polymorphic forms by X-ray structural analysis (X-ray diffraction pattern) given in Walter Levy, L.; Acad. Sc. Paris, t. 267 Series C, 1779 (1968). The β form is the most stable form, although conversions into the other forms are possible depending on the storage time and the ambient conditions. For commercial applications, it would therefore be desirable to obtain mannitol in the β form, owing to its stability, directly in the preparation, since the product properties change to the least possible extent due to storage in this case. In order to keep an active compound uniformly distributed in the preparation of pharmaceutical formulations, in particular in pulverulent formulations, it is desirable to bind the active compound strongly in the excipient.

Of importance for the tabletting properties of pulverulent D-mannitol are on the one hand the polymorphic form in which it exists and on the other hand the manner in which the particle structure of the individual particles has been built up.

WO 97/38960 A1 describes that improved tabletting properties arise through partial or complete conversion of pulverulent D-mannitol from the δ form into the β form. Conversion from the δ form into the β form can be caused by targeted wetting of the particle surfaces of the powder with a polar water-soluble solvent or with water and by subsequent drying. The percentage of β-mannitol formed is dependent on the amount of solvent employed and the duration of the drying operation. A mixture of δ and β forms is therefore usually present in the product.

Disadvantages of this process are that the conversion is an additional process step which follows the actual powder preparation, the drying requires at least 8 hours, during which the plant has to be continuously supplied with thermal energy, and that to date no targeted control possibility is known by means of which mannitol is obtained with a very high proportion in δ form.

The object of the present invention is therefore to provide a process which can be carried out in a simple manner and by means of which a granular, directly compressible mannitol in the β modification can be prepared in a single working step.

The object is achieved by a process for the preparation of directly compressible mannitol having a content of the δ modification of greater than 90%, characterised in that
  a) in a first step, an aqueous D-mannitol solution as starting material, spray gas, pulverulent δ-mannitol and hot gas are combined,
  b) the fine-grained granular material formed falls into a fluidised bed, is taken up, fluidised, and transported further.

Some of the granular product formed can be recycled into the process. This recycling of product formed is particularly advantageous if more than 90% therein is in the δ form.

The mannitol fed in at the beginning in the process, having a content of the δ modification of greater than 90%, may originate from a conventional preparation of δ-mannitol by crystallisation, where, however, a small particle size, which can be maintained by grinding and sieving, should be ensured. Only later after equilibrium has been achieved in the plant, where mannitol having a content of δ modification of greater than 90% is obtained continuously in the process, does the particle size play only a minor role.

In a particular embodiment of the process, the granular material formed can be, in one or more granulation step(s), sprayed with further liquid medium, dried and transported further in the fluidised bed.

For the preparation of the mannitol solution, use is made of D-mannitol having a purity of >90%, preferably >95%. Use is particularly preferably made of D-mannitol having a purity of >98%.

Surprisingly, the equilibrium can be shifted towards the formation of δ-mannitol by recycling δ-mannitol formed as the dust fraction from the product discharge zone of the processor into step a) of the spray drying. In a particularly advantageous embodiment of the process, δ-mannitol dust having a mean particle size of less than 20 μm, in particular having a mean particle size in the range from about 1 to 20 μm, preferably in the range from 3 to 15 μm, is recycled.

The recycling of "formation of δ-mannitol, which is formed as product discharge in the metering device in line (9A), is effected by controlling the rotational speed of the star valve 10A via the fan (E) into the spray drying of process step a). This means that the granular material from product recycling is ground to a powder in the grinding fan.

After the equilibrium has been established, it is easily possible to recycle pulverulent δ-mannitol having a mean particle size of less than 75 μm, but in particular also pulverulent unground δ-mannitol (9B, 10B).

Since a solid having special properties is generated in the process according to the invention, or spray-drying process from a solution or suspension, a distinction will be made here between the various solid forms granular material, powder and dust.

If the term granular material is used here, this is a granular, readily pourable solid having a specific structure, as the δ-mannitol prepared in accordance with the invention has. A granular material thus consists of solid and dry grains, where each grain in turn represents an agglomerate comprising particles having sufficient strength in order to allow various handling operations. If, by contrast, the term powder is used, these are solids comprising solid, loose, dry and more or less fine particles, preferably very fine particles, which are obtained by grinding the granular material prepared in accordance with the invention using a grinding fan. These particles do not have a specific structure since this has been destroyed during grinding.

Dust in turn consists of very fine particles which do not settle in air or only do so with difficulty (<10 μm), here an extremely fine solid formed in accordance with the invention from the gas phase (between fluidised bed and filter) of the processor. The particles are so fine that they cannot sediment.

The particular design of the plant used enables the recycled granular material to be comminuted, before the recycling, by grinding in the fan [(E), FIG. 2], which simultaneously serves as conveying element for the powder recycling.

Regulation of the rotational speeds of the star valves 10A and 10B (FIG. 2) of the plant used and grinding of the coarse (oversize) product formed to particle sizes of less than 75 μm in the fan [(E), FIG. 2] before recycling into the spray drying result in the exclusive formation of β-mannitol.

In order to carry out the process, an aqueous 40-50% D-mannitol solution (based on the weight of the entire solution) is employed as starting material and is atomised with a temperature in the range from 60 to 100° C.

Air or an inert gas selected from the group consisting of $N_2$ and $CO_2$ can be used both as spray gas and as carrier and heating gas. The gas is preferably circulated in the process according to the invention, and the circulated gas is freed from particles by filters, dried in the condenser and fed back to the spray nozzles or heated and introduced into the fluidised bed.

The circulated gas is preferably freed from particles with the aid of dynamic filters.

In a particular embodiment of the process, the liquid media used have different compositions at different points of the plant.

Particle sizes of between 50 and 1000 μm can be produced specifically in the process according to the invention by varying the process parameters of spray pressure, spray amount, mannitol concentration, amount of powder recycled, hot-air stream and hot-air temperature.

For this purpose, the air fed to the plant is, in accordance with the invention, pre-heated to a temperature in the range 45-110° C. and the amount of feed air supplied is set in the range 1000-2000 $m^3/m^2$ per hour, giving a waste-air temperature in the range 30-50° C. At the same time, the spray pressure of the two-component nozzles is set in the range 2-4 bar, so that from about 1.5 to 3 $m^3$/(h kg of solution) of hot gas are fed to the two-component nozzle, with the temperature of the hot gas being set in the range from about 80 to 110° C. Good process results are obtained if the recycling of powder and granular material is regulated in such a way that recycling is carried out in an amount in the range 0.5-2.0 kg of solid/(h kg of solution).

Particularly uniform formation of granular powder having a δ-mannitol content of >95% is carried out by adjustment of the parameters of spray pressure, amount of liquid, mannitol concentration, recycled amount of powder and granular material, hot-air stream and hot-air temperature, through which the amount of powder present in the fluidised bed is set to an amount in the range 50-150 $kg/m^2$ of bed.

By means of corresponding experiments, a process has been developed for the preparation of pure δ-(D)-mannitol by means of which directly compressible mannitol (DC mannitol) having a suitable homogeneous particle size distribution can be prepared. The process is carried out using mannitol having a purity of greater than 98%, where the remainder can be sorbitol and other residual sugars. An aqueous solution having a mannitol content of about 40-50% by weight is prepared. This solution is atomised in a spray-drying plant at a feed-air temperature of about 60-95° C. and dried.

The process is carried out using a slightly modified plant as described in DE 1 99 27 537. By means of the plant described in this patent application, it is possible per se to vary as desired the properties of spray-dried and granulated products with respect to particle size, particle size distribution, moisture content and compressibility. However, the plant modifications carried out enable additional fine adjustment through the recycling of powder and granular material.

In particular, the process is carried out in a spray-drying plant which comprises
  a) a spray-drying unit (B),
  b) a fluidised bed (A),
  c) one or more additional spray or atomisation nozzles for liquid media (C),
  e) a metering device (D) for product recycling and
  f) a powder and granular material recycling system (9) with fan (E),
where the lines (9A) and (9B) intended for recycling of powder and granular material are provided with star valves (10A, 10B), and the product (8) which does not enter the powder-metering device can be separated into a dust-form fraction and a coarse fraction by classification. Depending on demand and stage of equilibrium establishment of the process, the fan (E) can be fed either with dust-free feed air via flap (J) or dust-containing feed air via flap (H) (see FIG. 2).

In the spray-drying unit (B) of the plant used in accordance with the invention, the liquid medium (5), spray gas (6), pulverulent material (9) and hot gas (4) are combined.

In a particular embodiment, a spray-drying unit (B) is located vertically above a subsequent fluidised bed in a spray tower.

In a particular embodiment, the spray-drying unit (B) of the plant can comprise a spray system which consists of a two-component spray nozzle heated by means of hot water with coaxially arranged recycling of powder and granular material and surrounding hot-gas flow.

In the plant used, one or more additional spray or atomisation nozzles for liquid media (C) can be installed in the fluidised bed, also with variable location. The fluidised bed is followed by a powder-metering device (D), which is separated off by a valve flap (F) and which is fed by a product overflow (8). Some of the product formed can be recycled into the spray-drying unit (B) via fly conveying, in which a fan (E) serves as conveying element, after comminution (9A, 10A) or also without comminution (9B, 10B), if the equilibrium has been established. The fan (E) acting as conveying element can simultaneously serve as comminution unit for recycled powder.

In the process for the preparation of spray-dried granular δ-(D)-mannitol,
a) in a first step, a liquid medium, spray gas, pulverulent material and hot air are combined,
b) the granular product formed falls into a fluidised bed, is taken up, fluidised and transported further, and, if desired,
c) in one or more granulation step(s), sprayed with further liquid medium, dried
d) and conveyed in the fluidised bed in the direction of the metering device, from which
e) a part amount, ground or unground as pulverlulent or granular material, is recycled into the process.

The liquid medium is preferably an aqueous solution. However, it is also possible to employ a solution in which a water-soluble solvent has been employed or a solvent mixture which consists to a certain proportion of water In a particular variant of the process, the recycled material can be comminuted before the recycling.

The spray, carrier and heating gas used can be air or an inert gas selected from the group consisting of $N_2$ and $CO_2$. The gas can, in accordance with the invention, be circulated, it being freed from particles by filters or especially with the aid of dynamic filters, dried in the condenser and fed back to the spray nozzles or heated and introduced into the fluidised bed.

In order to carry out the process for the preparation of δ-(D)-mannitol in the form of a granular material in a fluidised bed, δ-mannitol is initially introduced as described above, or a fluidised bed of this type is produced from very finely divided β-mannitol powder. To this end, DC β-mannitol must be initially introduced as a bed in the processor. The DC β-mannitol has very similar mechanical properties to the DC δ-mannitol to be prepared, the start-up process is consequently more stable than a start with crystalline δ-mannitol (see FIG. 3). In order to obtain the desired δ-mannitol, the following parameters must be set in the process:

Temperature in the processor: max. about 35-45° C.
Spray pressure: max. 2.5-3.0 bar
Powder recycling: about 3 times the amount, based on the amount of product removed from the process
The recycled powder is not ground!
The powder takes route 9B/10B (the route via 9A/10A has been closed!)
Mannitol content: >98% by weight At this point, it is crucial that the grinding fan feed air is dust-free. In this case, flap (H) in the plant has been closed and flap (J) has been opened. The air is removed from the processor exhaust air after filters (G). In this setting, the formation of δ-mannitol commences and takes the course as shown in FIG. 3. At the beginning of the continuous process, the formation of δ-mannitol takes place in small amounts. Under the conditions set, as described above, the concentration increases continuously until it is about 95% by weight after an operating time of about 70 hours. The concentration of δ-mannitol subsequently only increases slightly and can have a value of greater than 98% by weight. If the content of δ-mannitol is plotted against the operating time, an S curve is obtained, as shown in FIG. 3.

When carrying out the process, it has been found that the process must be switched over when the content of δ-mannitol in the product formed has increased to about 60-70% by weight. From this time, the process must be switched over to recycling of dust-containing feed air, as depicted in FIG. 2. In this case, flap (H) in the plant has been opened and flap (J) has been closed. Only under these conditions can the content of δ-mannitol increase to greater than 90% by weight in the product.

In order to be able to prepare δ-mannitol which is stable in the continuous process according to the invention with such a high concentration, air containing extremely fine dust (fine mannitol dust) must be employed as feed air for the grinding fan and the parameters described above must be maintained. If these values are exceeded or not reached, the process slips out of the equilibrium, and β-mannitol again preferentially forms. Furthermore, the product formed must be dried to a residual moisture content of less than 1%, in particular less than 0.3%, in order to obtain a stable, storable product, since water converts δ-mannitol into the β modification.

In order to start up the process, the plant is charged at the beginning with pulverulent starter material via the fill ports (3). A stream of air is produced in the spray-drying space via the chambers (1). The introduced starter material is fluidised by this stream of air and moves in the direction of the discharge flaps (F). The product stream attains this direction of movement on generation of the air stream through a corresponding perforation of the Conidur plate. The fluidised product can be discharged by simply opening the valve flaps (F). At this point of the plant, devices are provided which enable the product to be recycled into a metering device and a fly conveyer to the spray-drying unit. An overflow (8) for the finished product is located at the discharge above the metering device. The fan (E) of the spray-drying unit serves as conveying means both for product recycling and as comminution unit for powder material to be recycled. The fan (E) receives the feed air either loaded with dust via flap (H) or dust-free via flap (J). Recycled powder and granular material from the return line (9A, 9B) is combined with the corresponding media liquid (5), spray air (6) and hot air (4) through the particular design of the spray-drying nozzle. The corresponding powder or granular material is taken up by the fluidised bed and, as already described above, transported further. On passing through the granulation nozzles (C), further medium, which can have a different composition to that introduced into the spray nozzle with powder recycling, can be sprayed onto the particles formed. In this way, further granulation and re-setting of the particle size distribution can take place. The product from the chambers (1) is dried to the desired final moisture content by means of air introduced via the Conidur plates. Dynamic filters (G) integrated into the plant prevent discharge of powder particles into the environment.

Instead of the granulation nozzles (C), as shown in FIG. 2, one or more spray nozzles or spray-drying nozzles or alternatively only one, two or more than three granulation nozzles can be installed at the corresponding point of the plant. These additional nozzles may be located directly at the beginning of the fluidised bed or moved further to the back. The choice of site at which the product originally formed is re-sprayed one or more times is, inter alia, also dependent on the residual moisture content that the desired product is to have. It goes without saying that a product having a particularly low residual moisture content after the final spraying makes a longer residence time in the fluidised bed necessary than one having a higher residual moisture content.

As desired, different compositions can be applied through the various nozzles to the particle surfaces already formed, enabling particles having a layered structure to be obtained. However, it can also serve to achieve a more uniform particle size distribution.

It is furthermore possible to operate the plant not only with air as carrier medium. It is also possible to operate the entire plant in circulation with an inert gas, such as, for example, nitrogen or carbon dioxide.

The plant is designed in such a way that the parameters amount of liquid, spray pressure, amount of powder and granular material recycled, amount of hot gas, hot-gas temperature, amount of warm air, warm-air temperature, etc., can be regulated individually. The amount of powder recycled, the amount of liquid fed in and the spray pressure can therefore be set specifically depending on the desired properties with respect to moisture content, particle size and particle size distribution of the end product. As desired, products having particle sizes of between 50 and 1000 μm can be produced in the plant described. Depending on the mode of operation and the process parameters selected, the particles can have a layered (onion) structure or an agglomerate structure.

The formation of the particles can be controlled particularly by a spray nozzle integrated into the plant, which is suitable for the production of spray-dried granular material. This spray nozzle is a spray system (B) which consists of a two-component spray nozzle [(1), (2), (3)], which can be heated by means of hot water and which is in turn equipped with a powder and granular material recycling system (4) arranged around the two-component spray nozzle and a surrounding hot-gas flow (5). Specifically, the powder and granular material recycling system (4) can be arranged coaxially around the two-component spray nozzle.

The advantage of this spray system is that recycled solid comes into contact immediately at the exit of the two-component spray nozzle with the liquid droplets generated via the atomisation air. In order that the particles do not stick together and that the surface moisture can be dissipated, the spray nozzle and the powder and granular material recycling system is enveloped in a stream of hot gas. Subsequent drying to the desired residual moisture content takes place in the fluidised bed.

In particular also through the incorporation of this spray-drying system, it is possible to produce particle sizes specifically.

A particular advantage of this spray-drying process therefore consists in that δ-(D)-mannitol having very different properties with respect to moisture content, particle size and particle size distribution in the powder can be prepared in a single plant without further process steps for aftertreatment of the product depending on the process parameters set and on the liquid media to be atomised.

In order to obtain particularly good DC properties (DC=direct compression) of the spray-dried substance, here mannitol, it is advantageous to agglomerate the individual particles formed in the spray drying. For this purpose, a spray tower (B) is located vertically above the fluidised bed.

The hot aqueous mannitol solution is atomised via one or more two-component nozzle(s) (5) (6), which is (are) heated with hot water (7). The spray jet produced is surrounded by a mannitol powder and granular material recycling system comprising (9) arranged around this nozzle and a stream of hot gas (4). The solid crystallises in the spray jet, forms agglomerates and is taken up by the fluidised bed. Hot air from the air introduction chambers (1) flows through the fluidised bed and fluidises the latter. The base of the fluidised bed is a Conidur plate, which ensures specific transport of the solid to the discharge and also produces a defined residence time of the solid in the fluidised bed. The residence time of the product in the processor can be controlled via the bed depth, spray amount and recycle quantity. The solid is transported through a plurality of air introduction chambers (1) connected in series and dried to a residual moisture content of <0.3%. The drying operation takes place over the length of the fluidised bed in a certain temperature profile in order to prevent overheating of the product.

The water-laden and dust-containing fluidisation air is cleaned via dynamic filters (G) and discharged via the waste-air chambers (2). The dynamic filters are regularly cleaned by means of pulses of compressed air. The dust cleaned off binds the spray mist from the spray zone and prevents baking onto the walls.

The dried solid falls into a metering system for recycling (D) via double pendulum flaps (F) or other discharge systems. The discharged product can optionally be worked-up further via a classification system. The oversize particles (and undersize particles) formed can be ground in the fan (E) above the powder recycling system (9) and recycled into the spray drier together with the undersize particles (dust-form mannitol powder having particle sizes of less than 75 μm, in particular less than 40 μm).

A part-stream is discharged at the outlet as finished product (8). The product can be classified via a sieve, it being possible for the oversize particles (residual material, or coarse powder fraction) to be recycled via the suction side of the grinding fan (9A), ground and returned to the process. Inter alia, this minimises product losses.

The fan (E) of the spray-drying unit serves both as conveying means for product to be recycled (introduction of solid on the pressure side (9B)) and as comminution unit for recycled powder material (introduction of solid on the suction side (9A)). The two part-streams of solid are controlled, for example, via the rotational speed of the star valves (10A, 10B). Recycled powder and granular material from the return lines (9) is, as already described above, combined with the corresponding media liquid (mannitol solution) (5), spray air (6) and hot air (4) through the particular design of the spray-drying nozzle.

Feed air is fed to the fan (E) from the product discharge zone of the processor when flap (H) has been opened and flap (J) has been closed. In this way, the fine dust (<15 μm) is removed from the product at the same time (pneumatic classification). At the same time, the removal of this fine dust has the effect that greater tablet hardness values can be achieved on use of this product freed from fine dust.

In the case of part-stream 9B, the option exists of screening the oversize particles (residual material) out of the recycling system after the star valve 10B in order to be able to control the process better. These oversize particles (residual material) can be introduced on the suction side into the grinding fan (E) or another comminution machine, ground and fed back to the process.

As already indicated above, the quality of the agglomerates and thus of the product can be controlled via the plant parameters, such as concentration, spray pressure, temperature, spray amount, amount of recycled powder and granular material, amount of principal air, dust extraction, bed depth, etc. A reduction in the height of the spray nozzle [(B)→(C)] above the fluidised bed enables the particle structure to be converted from an agglomerate (berry structure) into a granular material (onion structure). At the lowest possible arrangement of the nozzles (granulation nozzles (C)), the powder recycling (9) can take place via the fill ports (3). In order to obtain a directly compressible product continuously, both the particle structures, but also the modification, particle size distribution, water content, density, etc., must be monitored. It has been found that the best tablettable product is obtained if mannitol is crystallised out in a fine needle structure.

Contamination by other mannitol modifications in the granular mannitol impairs the tabletting properties. In particular, it has been found that, especially, increasing contents of α-mannitol have an adverse effect on the compressibility, the achievable tablet hardness values and the surface quality of the tablets. In products produced by the process according to the invention, no α-mannitol per se can be detected, in particular in mannitol which has a content of the δ modification of greater than 95% by weight, in particular greater than 98% by weight.

FIG. 1 shows an SEM photograph of a product having a content of the δ modification of greater than 98% in 500× magnification.

Experiments have shown that it is necessary to maintain and monitor the set parameters of the spray-drying process in order to obtain pure δ-mannitol which has constant, readily compressible properties.

In accordance with the invention, the starting material employed is preferably D-mannitol having a purity of >90%, particularly preferably having a purity of >95% and very particularly preferably having a purity of >98%. This starting material is employed in the form of an aqueous 40-50% solution and is atomised into the plant at a temperature in the range from 60 to 95° C. The solution is preferably heated to a temperature in the range from 70 to 85° C., in particular from 75 to 80° C., before the atomisation.

In accordance with the invention, solutions having different mannitol concentrations can be employed at different points of the plant. Thus, it has proven appropriate to charge spray nozzles above the fluidised bed in the direction of the product discharge with solutions having higher mannitol concentrations than spray nozzles located at the beginning of the fluidised bed. It is therefore possible to employ a solution having a mannitol concentration of about 60% by weight, based on the solution as a whole, at the end of the fluidised bed, whereas the two-component nozzle with powder recycling is preferably operated with an approximately 40-50% aqueous solution. In this way, the product properties can again be influenced in the desired sense, it being necessary to observe the plant parameters precisely in this procedure.

Through variation of the parameters spray pressure, amount of liquid, amount of powder recycled, hot-air stream and hot-air temperature, particle sizes of between 50 and 1000 μm can be set specifically.

It has furthermore been found that the parameters of the plant used in accordance with the invention have to be set as follows in order to obtain a uniform product:

The spray pressure of the two-component nozzles should be set in the range 2-4 bar, preferably in the range from 2.5 to 3.5 bar.

The feed of hot gas at the top of the plant can support the process of the formation of δ-mannitol.

The amount of hot gas fed to the two-component nozzle should be regulated in such a way that from about 1.5 to 3 m$^3$/(h kg of solution) at a temperature of from about 80 to 110° C. are conveyed. It has been found that, with a relatively large amount of hot gas feed, better product quality is obtained if a relatively low temperature is used.

The recycling of the solid should be set in accordance with the invention in such a way that recycling takes place in the range 0.2-2.0 kg of solid/(h kg of solution), preferably in the range from 0.5 to 1.5 kg of solid/(h kg of solution). The process is particularly favourable if the solids recycling is in the range from 0.5 to 1.0 kg of solid/(h kg of solution).

In order to carry out the process, pre-heated air must be fed into the plant. Good results are achieved if the air fed to the plant is pre-heated to a temperature in the range 45-120° C. It is favourable for the process according to the invention if the feed air has a temperature in the range from 65 to 110° C. It is particularly advantageous for the formation of a δ-mannitol granular material having good tabletting properties if the temperature of the feed air fed in is in the range from 70 to 100° C.

The amount of feed air supplied should be regulated in accordance with the invention in such a way that 1000-2000 m$^3$/m$^2$ per hour, in particular from 1200 to 1700 m$^3$/m$^2$ per hour, are fed into the plant.

In combination with the other parameters set, favourable process conditions exist if the air stream in the plant is set in such a way that the waste-air temperature is in the range 30-50° C.

It has furthermore proven favourable to regulate the process conditions in such a way that the amount of solid located in the fluidised bed is set to an amount of 50-150 kg/m$^2$ of bed. It is particularly favourable if the amount of powder is in the range 80-120 kg/m$^2$ of bed.

It has also been found that the process can be controlled, in particular, by specific recycling of the solid having a selected particle size.

It has been found in spray experiments that the formation of δ-mannitol from β-mannitol is only obtained if the grinding fan feed air is dust-free, i.e. flap (H) has been closed and flap (J) has been opened, and the feed air can be drawn, for example, directly from the processor above the process filter, or temperature-controlled and conditioned fresh air is employed. In order to keep the spray process stable, solid granular material from the processor must be recycled with the aid of the grinding fan. The granular material is introduced both upstream and downstream of the grinding fan, the ratio between ground powder and unground granular material can be adjusted by adjusting the rotational speed of the star valves 10A and 10B. When a δ-mannitol content of significantly greater than 50%, better a content of 60-70%, has formed in the bed, the grinding fan feed air must be switched over from dust-free to dust-containing feed air from the processor. In this case, flap (H) has been opened and flap (J) has been closed. The δ-mannitol content thus increases further to greater than 90%, in the case of an extended process duration; i.e. with the parameters set, the content even increases to greater than 95% and even reaches values of greater than 98%.

As can be seen from the plant diagram, recycling of solid can be carried out both by withdrawal of solid from the fluidised bed and by recycling of a very finely divided solid fraction which is formed during finishing, i.e. during homogenisation of the particle size by screening and packaging of the resultant product.

It is also possible, prior to recycling, to comminute solid having relatively large particle cross sections in the fan (E) of the spray-drying unit to give a powder. As already indicated above, the powder stream can be controlled by adjusting the rotational speed of the star valves (10A, 10B). In order to grind solid to be recycled to the desired particle size before the recycling, the rotational speed of the star valve 10A (B) should accordingly be set in such a way that recycling takes place via the fan with grinding.

Experiments have shown that the equilibrium can be shifted towards the formation of δ-mannitol if the mean particle size of the recycled powder ground in the fan (E) is less than 75 μm. δ-mannitol is particularly preferably formed if the mean particle size of the recycled powder is less than 40 μm. Surprisingly, it has been found that recycling of a powder having particle sizes of less than 20 μm gives mannitol powders having a proportion of the δ fraction of greater than 90%.

It has particularly surprisingly been found that, in particular, recycling of the so-called dust fraction which is formed in the product discharge zone of the processor and is usually removed from the product, results in a uniform product having a particularly high proportion of the δ fraction. The mean particle size of the dust fraction is in the range from about 1 to 20 μm, in particular in the range from 3 to 15 μm. In addition, it has been found that the dust from the recycling results in stable operation in the spray zone of the processor.

Since grinding in the fan (E) only gives these particle sizes with particular effort, the "dust-form" product fraction from the powder-metering device, which is formed in the plant in line (9A), is preferably recycled into the spray drying, in particular at the beginning of the process, by controlling the rotational speed of the star valve 10A by grinding. By simultaneously reducing the rotational speed of the star valve 10B, recycling of coarse mannitol fraction is reduced.

Surprisingly, it has been found that, after the equilibrium has been established in the direction of the formation of δ-mannitol in a proportion of more than 90% in the product, the process can be continued in a stable manner in the process if the powder ground in the fan to a particle size of less than 75 μm is likewise recycled.

In this way, it is possible, surprisingly, to set the spray-drying process by exclusive recycling of the "powder fraction" formed by regulation of the rotational speeds of the star valves 10A and 10B in such a way that the sole formation of δ-mannitol takes place. The relatively coarse fraction (the so-called oversize particles) of the mannitol granular material formed can subsequently again also be recycled into the process without risking shifting the equilibrium. This has the advantage that adhesion of particularly finely divided spray mist to the walls of the plant in long-term operation can be avoided and interruptions to the process can be prevented.

A suitable choice of the process parameters thus enables production of a product having a content of the δ modification of greater than 90%. Constant monitoring of the product quality produced enables the fraction to be increased readily to a content of the δ modification to greater than 95%.

In particular in the case of optimum setting the above-described plant parameters and monitoring of the other process parameters, the product obtained in the process according to the invention is a mannitol having the following properties:

directly compressible mannitol
purity of the δ modification>98%
bulk density 350-500 g/l
residual moisture content <0.3%
particle distribution: $x_{50}$ at 200 μm: <10%<53 μm+<15%>500 μm $x_{50}$ at 300 μm: <10%<100 μm+<10%>850 μm $x_{50}$ at 450 μm: <5%<100 μm+<10%>850 μm Since the various modifications of the mannitol are very similar, they cannot be differentiated in the DSC on the basis of their melting points usually measured in analysis. Identification is only possible, for example, by means of X-ray or NIRS.

However, owing to the tablet hardness values achieved with the resultant product, significant differences from commercially available products are evident. Compared with a commercially available crystalline product, tablets having hardness values which are from about 45 to 70% higher are obtained with the δ-mannitol prepared in accordance with the invention.

TABLE 1

Tablet hardnesses using mannitol from various preparation processes as excipient material

| | δ-Mannitol crystallisation | δ-Mannitol spray-dried | β-Mannitol spray-dried |
|---|---|---|---|
| Flowability | poor | good | good |
| Tablet hardness (pressure 20 kN) | Approx. 100N | Approx. 260N | Approx. 260N |
| Tablet hardness With added binder (pressure 20 kN) | Approx. 140N | — | — |

It has been found that the mannitol in the form of a granular material having a content of the δ modification of greater than 90% can be used in a simple manner to bind a pharmaceutical active compound strongly to the grain or into the granule grain in the presence of moisture or a suitable solvent during conversion of the crystal structure from the β form into the δ form. In this way, for example, pulverulent active-compound formulations can be prepared very well by spraying the product according to the invention into a fluidised bed in a controlled manner with an active-compound-containing solution or suspension at a suitable temperature. During drying, δ-mannitol can be converted into β-mannitol, where the sprayed-on active compound is likewise included in the granular material and the crystals building up the granular material.

For better understanding and in order to illustrate the invention, a general flow chart of the structure (FIG. 2) of the spray-drying plant described is given below, along with examples which are within the scope of protection of the present invention, but are not suitable for restricting the invention to these examples.

FIG. 2 shows a generalised flow chart of a possible embodiment of a spray-drying plant employed for carrying out the process, in which the numbers and letters given have the following meanings:

1 Air introduction chambers
2 Heating devices
3 Fill ports
4 Hot-air feed
5 Liquid feed
6 Spray air
7 Heating medium
8 Product
9 Powder
(9A finely divided powder (dust), 9B coarse granular material)
10 Star valve (10A and 10B) for regulating the powder recycling
A Fluidised-bed apparatus
B Spray-drying unit
C Granulation nozzles
D Solid-metering device
E Fan for recycling of powder and granular material
F Valve flaps
G Dynamic filter
H Feed-air flap for dust-containing gas
J Feed-air flap for dust-free gas With reference to the components mentioned in the description and given in the flow chart, it is readily possible for the person skilled in the art to produce an appropriate plant for carrying out the process by selecting commercially available individual components. It goes without saying for the person skilled in the relevant art that both additional electrical and mechanical control units have to be installed for operation of the plant in order to be able to regulate and vary the parameters in the process according to the invention, as described.

In order to illustrate the present invention, the following figures are attached to the description:

Figure 1:
FIG. 1: SEM photomicrograph of a product having a content of δ modification of greater than 98% in 500-times magnification.
Figure 2:
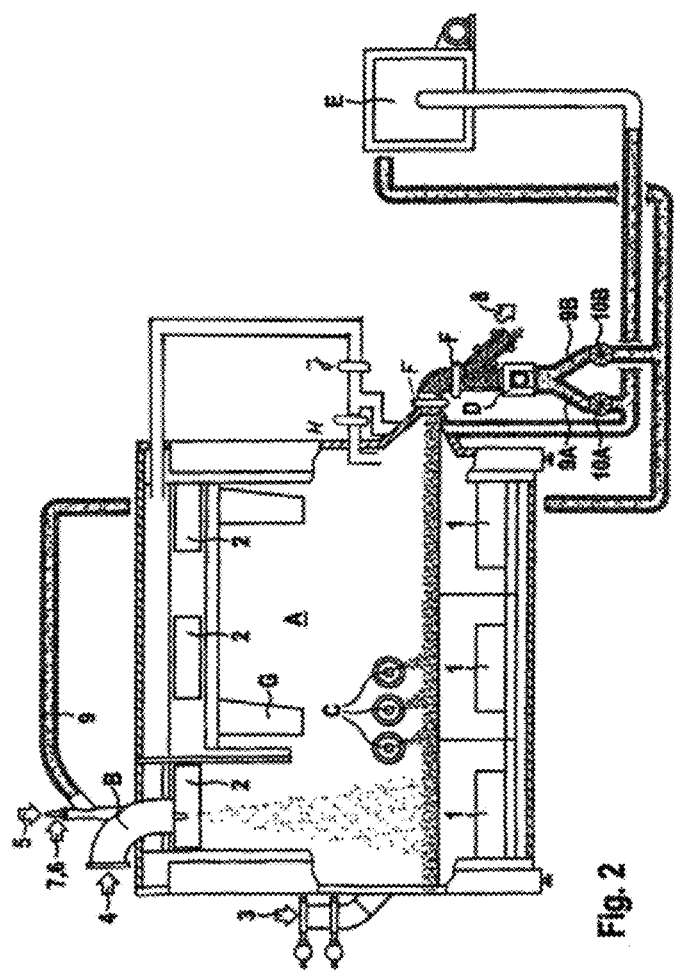
FIG. 2: Generalised flow chart of a possible embodiment of a spray-drying plant employed for carrying out the process
Figure 3:
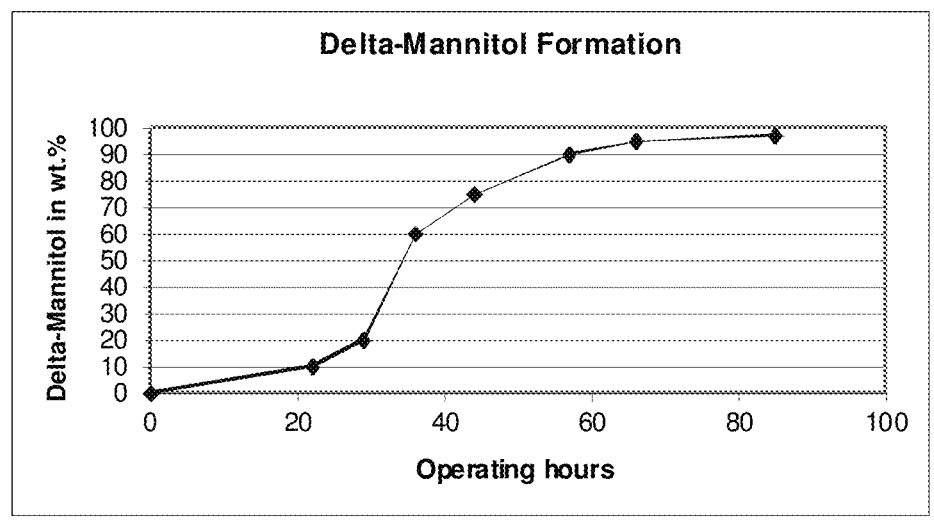
FIG. 3: Plot of the against the content of δ-mannitol Furthermore, the references and patent specifications cited in the description should also be used for better understanding, if anything is unclear, and are hereby incorporated into the description of the present invention as part of the disclosure content.

The temperatures given in the examples and description and in the Claims are always in ° C. Unless indicated otherwise, content data are given as % by weight or weight ratios.

Furthermore, it goes without saying to the person skilled in the art that, both in the examples given and also in the remainder of the description, the component amounts present in the compositions always add up only to 100% by weight or mol-%, based on the composition as a whole, and cannot exceed this, even if the per cent ranges indicated could give rise to higher values. Unless indicated otherwise, % data are regarded as % by weight, with the exception of ratios, which are indicated in volume data.

The following examples for the preparation of various DC δ-mannitol grades serve to explain the present invention in greater detail.

EXAMPLE 1

Preparation of a DC δ-Mannitol Having a Mean Article Size $X_{50}$=200 µm

For preparation, the spray-drying plant is filled with about 70 kg/m² of δ-mannitol as the bed. (This initially introduced bed should as far as possible have the desired product properties. If the bed material available should have other properties, the plant must be started up under gentle conditions until the equilibrium has shifted in the desired direction.)

As fluidisation and feed air, the plant is operated with 1200 m³/m² h at a temperature of about 70° C. (Before start-up of the plant, it must be ensured that sufficient dust is present in the plant. Dust can be generated via the powder-metering device (D) and blown into the plant through product formed being transported from the suction-side recycling system (9A) and metering device (10A) via the by means of the fan (E) and ground). The feed air to the fan (E) is introduced via flap (H). When sufficient dust is in the plant, the metering (10A) of the recycle can be reduced, and the atomisation of mannitol solution is begun. The atomised solution has a concentration of about 40% and a temperature of about 75° C. At a spray pressure of about 3 bar (spray medium is air), about 45 kg/m² h of solution are atomised in the plant. About 0.5 kg of solid/(h kg of solution) is recycled into the spray zone via the recycling system (9, 10) via the powder-metering device (D). The star wheels (10A, 10B) are set in such a way that a sufficient amount of product (9A, 10A) is always ground in the fan (E) and conveyed back into the plant with the unground product (9B, 10B).

Evaporation of the water in the plant causes the formation of an equilibrium with a bed temperature of about 35-40° C. The waste-air temperature is about 30-33° C. (It must be ensured that the waste air is saturated as far as possible (about 80-90% rel. humidity). This is advantageous for the efficiency of the process and for the mannitol crystallisation process.) In this way, the best crystal structure and the purest β modification of the mannitol are obtained. Since the fan (E) takes its feed air from the product discharge zone before the valve flaps (F) of the plant (A), and the discharged product is thus low-dust due to the pneumatic classification, δ-mannitol having excellent properties for direct compression is obtained at the product outlet (8). In order to obtain DC δ-mannitol having the desired particle size distribution, it can be sieved after the discharge valve (F), i.e. before the product outlet (8) and the powder-metering device (D). It is advantageous for the process also to sieve the oversize particles out of the product to be recycled (9B, 10B), since they otherwise accumulate further in the spray zone and can cause problems in the fluidised bed. The undersize and oversize particles sieved out can be fed on the suction side to the fan (E), ground and fed back into the process together with the other recycled solids sub-streams (9A, 10A, 9B, 10B). In this way, product losses are minimised, and the process runs in a more stable manner through the additional dust recycling (ground product).

EXAMPLE 2

Preparation of a DC δ-Mannitol Having a Mean Article Size $X_{50}$=300 µm

As described in Example 1, the spray-drying plant is, for preparation, filled with about 100 kg/m² of δ-mannitol as the bed and started up.

As fluidisation and feed air, the plant is operated with 1500 m³/m² h at a temperature of about 85° C. The mannitol solution to be atomised has a concentration of about 45% at a temperature of about 80° C. At a spray pressure of about 3 bar (spray medium is air), about 65 kg/m² h of solution is atomised in the plant. The star wheels (10A, 10B) are set in such a way that a sufficient amount of product (9A, 10A) is always ground in the fan (E) and conveyed back into the plant with the unground product (9B, 10B). The feed air to the fan (E) is introduced via flap (H).

Evaporation of the water in the plant causes the formation of an equilibrium with a bed temperature of about 40° C. The waste-air temperature is about 35-40° C. It must be ensured that the waste air is saturated as far as possible (about 80-90% rel. humidity). The oversize particles from the product to be recycled (9B, 10B) are sieved out, since they otherwise accumulate further in the spray zone and cause problems in the fluidised bed. The undersize and oversize particles sieved out are fed on the suction side to the fan (E) and ground. They are fed back into the process together with the other recycled solids sub-streams (9A, 10A, 9B, 10B).

EXAMPLE 3

Preparation of a DC δ-Mannitol Having a Mean Article Size $X_{50}$=450 µm

As described in Example 1, the spray-drying plant is, for preparation, filled with about 120 kg/m² of δ-mannitol as the bed. As fluidisation and feed air, the plant is operated with 1700 m³/m² h at a temperature of about 100° C.

The hot gas is fed to the spray zone in an amount in the order of about 1.6 m³/(h kg of solution) at a temperature of about 80° C. When all these parameters have been set, atomisation of mannitol solution can be begun.

The solution has a concentration of about 50% at a temperature of about 90° C. At a spray pressure of about 3.5 bar (spray medium is air), about 100 kg/m² h of solution are atomised in the plant. Bed/product from about 0.8-1.0 kg of solid/(h kg of solution) is recycled into the spray zone via the powder-metering device (D) via the recycling system (9, 10). The star wheels (10A, 10B) are set in such a way that a sufficient amount of product (9A, 10A) is always ground in the fan (E) and conveyed back into the plant with the unground product (9B, 10B).

Evaporation of the water in the plant causes the formation of an equilibrium with a bed temperature of about 40-45° C. The waste-air temperature is about 40° C. It must be ensured that the waste air is saturated as far as possible (about 80-90% rel. humidity).

The oversize particles from the product to be recycled (9B, 10B) are sieved out since they otherwise accumulate in the spray zone and cause problems in the fluidised bed. The undersize and oversize particles sieved out are fed on the suction side to the fan (E) and ground. The feed air to the fan (E) is fed via flap (H). They are fed back into the process together with the other recycled solids sub-streams (9A, 10A/9B, 10B).

The invention claimed is:

1. Process for the preparation of directly compressible mannitol having a content of the δ modification of greater than 90%, characterised in that
   a) in a first step, an aqueous D-mannitol solution as starting material, spray gas, pulverulent δ-mannitol and hot gas are combined,
   b) the resultant granular product falls into a fluidised bed, is taken up, fluidised and transported further, and
   c) some of the product formed, optionally after prior grinding to a smaller particle size, is recycled into the process in a controlled manner.

2. Process according to claim 1, characterised in that, after establishment of the equilibrium, a product having a content of δ-mannitol of greater than 95%, in particular greater than 98%, is obtained.

3. Process according to claim 1, characterised in that the resultant granular material is, in one or more granulation step(s), sprayed with further liquid medium, dried and transported further in the fluidised bed.

4. Process according to claim 3, characterised in that the liquid media used have different compositions at different points of the plant.

5. Process according to claim 1, characterised in that, for the preparation of the mannitol solution employed, use is made of D-mannitol having a purity of >90%, preferably >95%, particularly preferably having a purity of >98%.

6. Process according to claim 1, characterised in that the equilibrium is shifted towards the formation of δ-mannitol by recycling the δ-mannitol formed as dust fraction from the product discharge zone of the processor into step a).

7. Process according to claim 6 characterised in that δ-mannitol having a mean particle size of less than 20 μm, in particular having a mean particle size in the range from about 1 to 20 μm, preferably in the range from 3 to 15 μm, is recycled.

8. Process according to claim 6 characterised in that the "dust-form" δ-mannitol formed in line (9A) is recycled into the spray drying (step a)) from the powder-metering device as pulverulent δ-mannitol by controlling the rotational speed of star valve (10 A) via fan (E).

9. Process according to claim 1, characterised in that, after establishment of the equilibrium, δ-mannitol having a mean particle size of less than 75 μm is recycled.

10. Process according to claim 1, characterised in that, after establishment of the equilibrium, unground δ-mannitol granular material is recycled.

11. Process according to claim 10, characterised in that the recycled solid material is comminuted to a powder, before the recycling, by grinding in fan (E), which simultaneously serves as conveying element for the solids recycling.

12. Process according to claim 1, characterised in that the formation of δ-mannitol takes place solely through the specific setting and regulation of the rotational speeds of star valves 10A and 10B and grinding of the coarse product formed to particle sizes of less than 75 μm in fan (E) before the recycling into the spray drying.

13. Process according to claim 12, characterised in that, in order to carry out the process, β-mannitol is initially introduced at the beginning in order to build up the fluidised bed.

14. Process according to claim 1, characterised in that an aqueous 40-50% D-mannitol solution is employed as starting material and is atomised at a temperature in the range from 60 to 95° C.

15. Process according to claim 1, characterised in that air or an inert gas selected from the group $N_2$ and $CO_2$ is used both as spray gas and as carrier and heating gas.

16. Process according to claim 1, characterised in that the gas is circulated, and the circulated gas is freed from particles by filters, dried in the condenser, optionally heated, and fed to the spray nozzles again and introduced into the fluidised bed.

17. Process according to claim 16, characterised in that the gas is freed from particles with the aid of dynamic filters.

18. Process according to claim 1, characterised in that particle sizes between 50 to 1000 μm are produced specifically by varying the parameters spray pressure, spray amount, mannitol concentration, amount of powder or granular material recycled, hot-air stream and hot-air temperature.

19. Process according to claim 18, characterised in that the air fed to the plant is pre-warmed to a temperature in the range 45-120° C., and the amount of feed air fed in is set in the range 1000-2000 m³/m² per hour, giving a exhaust-air temperature in the range 30-50° C.

20. Process according to claim 18, characterised in that the spray pressure of the two-component nozzles is set in the range 2-4 bar, and about 1.5 to 3 m³/(h kg of solution) of hot gas having a temperature of about 80 to 110° C. are fed to the two-component nozzle.

21. Process according to claim 18, characterised in that the solids recycling is carried out in an amount in the range 0.2-2.0 kg of solid/(h kg of solution).

22. Process according to claim 18, characterised in that the amount of powder present in the fluidised bed is set to an amount in the range 50-150 kg/m² of bed by adjustment of the parameters spray pressure, amount of liquid, mannitol concentration, amount of solid recycled, hot-air stream and hot-air temperature.

* * * * *